United States Patent [19]

Payne et al.

[11] Patent Number: 4,595,703
[45] Date of Patent: Jun. 17, 1986

[54] PREPARATION OF HYDROCARBONS FROM SYNTHESIS GAS

[75] Inventors: Virgil L. Payne; Charles H. Mauldin, both of Baton Rouge,, La.

[73] Assignee: Exxon Research and Engineering Co., Florham Park, N.J.

[21] Appl. No.: 626,023

[22] Filed: Jun. 29, 1984

[51] Int. Cl.$^4$ .............................................. C07C 1/04
[52] U.S. Cl. .................................. 518/715; 518/709; 385/638; 385/733
[58] Field of Search ........................................ 518/715

[56] References Cited

U.S. PATENT DOCUMENTS

| | | | |
|---|---|---|---|
| 2,244,573 | 6/1941 | Roberts | 518/715 |
| 2,450,500 | 10/1948 | Clark | 518/715 |
| 4,088,671 | 5/1978 | Kobylinski | 260/449 |
| 4,338,089 | 7/1982 | Schaper et al. | 518/707 |
| 4,385,193 | 5/1983 | Bijwarrd et al. | 585/310 |

FOREIGN PATENT DOCUMENTS 2073237  3/1981  United Kingdom ................ 332/385

OTHER PUBLICATIONS

Lisitsyn et al., Institute of Catalysis, Siberian Branch of the Academy of Sciences of the USSR, Novosibirisk Translated from Kinetkai Kataliz, vol. 23, No. 4, pp. 919-931, Jul.-Aug. 1982.
92:129385h; The Synthesis of Solid Hydrocarbons from Methanol; Shima, Kensuke, Morita, Tauyoshi (Miyazaki Univ., Miyazaki, Japan); Nouveau Journal De-Chime, vol. 6, No. 10-1982, p. 459.
Fischer-Tropsch Synthesis of Hydrocarbons Over Ruthenium Supported on Transition Metal Oxides; Kikuchi, Nomura, Matsumoto and Morita (Waseda University, Tokyo 160); Pan-Pacific Synfuels Conference, vol. I, Nov. 17-19, 1982 Tokyo, pp. 1-10.
Fischer-Tropsch Synthesis Over Titania-Supported Ruthenium Catalysts; Kikuchi, Matsumoto, Takahashi, Machino and Morita (Waseda University, 3-4-1 Okubo, Shinjuku, Tokyo, Japan); Printed in the Netherlands; Applied Catalysis, 10 (1984), pp. 251-260.

Primary Examiner—Howard T. Mars
Attorney, Agent, or Firm—Llewellyn A. Proctor

[57] ABSTRACT

A process wherein an admixture of carbon monoxide and hydrogen is contacted over a cobalt catalyst, especially a thoria promoted cobalt catalyst, formed by dispersing the cobalt, or cobalt and thoria, upon a titania or titania-containing support wherein the titania support is one having a rutile:anatase ratio of at least about 2:3, and preferably at least about 3:2 to produce, at reaction conditions, a distillate fuel constituted principally of an admixture of linear paraffin and olefins, particularly a $C_{10}+$ distillate which can be further refined and upgraded to high quality fuels, and other products such as mogas, diesel fuel, jet fuel, lubes and specialty solvents, particularly premium middle distillate fuels of carbon numbers ranging from about $C_{10}$ to about $C_{20}$.

24 Claims, No Drawings

PREPARATION OF HYDROCARBONS FROM SYNTHESIS GAS

BACKGROUND AND PROBLEMS

I. Field of the Invention

This invention relates to a process for the preparation of liquid hydrocarbons from synthesis gas. In particular, it relates to a process wherein $C_{10}+$ distillate fuels, and other valuable products, are prepared by reaction of carbon monoxide and hydrogen, over certain types of cobalt catalysts.

II. The Prior Art

Methane is often available in large quantities from process streams either as an undesirable by-product in admixture with other gases, or as an off gas component of a process unit, or units. More importantly, however, methane is the principle component of natural gas, and it is produced in considerable quantities in oil and gas fields. The existence of large methane, natural gas reserves coupled with the need to produce premium grade transportation fuels, particularly middle distillate fuels, creates a large incentive for the development of a new gas-to-liquids process. The technology to convert coal or natural gas to synthesis gas is well established, and the conversion of the synthesis gas to hydrocarbons can be carried out via Fischer-Tropsch synthesis.

Fischer-Tropsch synthesis for the production of hydrocarbons from carbon monoxide and hydrogen is now well known in the technical and patent literature. The first commercial Fischer-Tropsch operation utilized a cobalt catalyst, though later more active iron catalysts were also commercialized. An important advance in Fischer-Tropsch catalysts occurred with the use of nickel-thoria on kieselguhr in the early thirties. This catalyst was followed within a year by the corresponding cobalt catalyst, 100 Co:18 ThO$_2$:100 kieselguhr, parts by weight, and over the next few years by catalysts constituted to 100 Co:18 ThO$_2$:200 kieselguhr and 100 Co:5 ThO$_2$:8 MgO:200 kieselguhr, respectively. The Group VIII non-noble metals, iron, cobalt, and nickel have been widely used in Fischer-Tropsch reactions, and these metals have been promoted with various other metals, and supported in various ways on various substrates. Most commercial experience has been based on cobalt and iron catalysts. The cobalt catalysts, however, are of generally low activity necessitating a multiple staged process, as well as low synthesis gas throughput. The iron catalysts, on the other hand, are not really suitable for natural gas conversion due to the high degree of water gas shift activity possessed by iron catalysts. Thus, more of the synthesis gas is converted to carbon dioxide in accordance with the equation: $H_2+2CO \rightarrow (CH_2)_xCO_2$; with too little of the synthesis gas being converted to hydrocarbons and water as in the more desirable reaction, represented by the equation: $2H_2+CO \rightarrow (CH_2)_x+H_2O$.

There exists a need in the art for a process useful for the conversion of synthesis gas at high conversion levels, and at high yields to premium grade transportation fuels, especially $C_{10}+$ distillate fuels; particularly without the production of excessive amounts of carbon dioxide.

III. Objects

It is, accordingly, a primary objective of the present invention to supply this need.

A particular object is to provide a novel process useful for the conversion of synthesis gas, i.e., carbon monoxide and hydrogen to high quality distillate fuels characterized generally as admixtures of $C_{10}+$ linear paraffins and olefins.

IV. The Invention

These objects and others are achieved in accordance with the present invention embodying a process wherein an admixture of carbon monoxide and hydrogen is contacted over a cobalt catalyst, especially a thoria promoted cobalt catalyst, formed by dispersing the cobalt, or thoria and cobalt, upon a titania or titania-containing support wherein the titania is one having a rutile:anatase weight ratio of at least about 2:3, and preferably at least about 3:2 to produce, at reaction conditions, a distillate fuel constituted principally of an admixture of linear paraffin and olefins, particularly a $C_{10}+$ distillate which can be further refined and upgraded to high quality fuels, and other products such as mogas, diesel fuel, jet fuel, lubes and specialty solvents, especially premium middle distillate fuels of carbon numbers ranging from about $C_{10}$ to about $C_{20}$. The rutile:anatase ratio is determined by ASTM D 3720-78: Standard Test Method for *Ratio of Anatase to Rutile In Titanium Dioxide Pigments By Use of X-Ray Diffraction*.

The cobalt-titania catalyst, or thoria promoted cobalt-titania catalyst used in this process, is one wherein cobalt, or cobalt and thoria, is composited, or dispersed upon titania, $TiO_2$, or a titania-containing carrier, or support, wherein the support contains a rutile:anatase ratio of at least about 2:3, and preferably at least about 3:2. In its most preferred form the titania, or titania component of the carrier, or support, will contain a maximum of rutile $TiO_2$, as opposed to the anatase or other form of titania; generally a rutile:anatase ratio of from about 3:2 to about 100:1, or greater, and more preferably from about 4:1 to about 100:1, and greater. The cobalt, or cobalt and thoria, is dispersed on the support in catalytically effective amounts. Suitably, in terms of absolute concentration, the cobalt is dispersed on the support in amounts ranging from about 2 percent to about 25 percent, preferably from about 5 percent to about 15 percent, based on the total weight of the catalyst composition (dry basis). The thoria is dispersed on the support in amounts ranging from about 0.1 percent to about 10 percent, preferably from about 0.5 percent to about 5 percent, based on the total weight of the catalyst composition (dry basis). Suitably, the thoria promoted cobalt catalyst contains Co and ThO$_2$ in ratio of Co:ThO$_2$ ranging from about 20:1 to about 1:1, preferably from about 15:1 to about 2:1, based on the weight of the total amount of Co and ThO$_2$ contained on the catalyst. These catalyst compositions, it has been found, produce at reaction conditions a product which is predominately $C_{10}+$ linear paraffins and olefins, with very little oxygenates. These catalysts provide high selectivity, high activity and good activity maintenance in the conversion of carbon monoxide and hydrogen to distillate fuels.

In conducting the reactions the total pressure upon the reaction mixture is generally maintained above about 80 pounds per square inch gauge (psig), and preferably above about 140 psig, and it is generally desirable to employ carbon monoxide, and hydrogen, in molar ratio of $H_2:CO$ above about 0.5:1 and preferably equal to or above 2:1 to increase the concentration of $C_{10}+$ hydrocarbons in the product. Suitably, the $H_2:CO$ molar ratio ranges from about 0.5:1 to about 4:1, and preferably the carbon monoxide and hydrogen are employed in molar ratio $H_2$:CO ranging from about 2:1 to about 3:1. In general, the reaction is carried out at gas hourly space velocities ranging from about 100 V/Hr/V to about 5000 V/Hr/V, preferably from about 300 V/Hr/V to about 1500 V/Hr/V, and at temperatures ranging from about 160° C. to about 290° C., preferably from about 190° C. to about 260° C. Pressures preferably range from about 80 psig to about 600 psig, more preferably from about 140 psig to about 400 psig. The product generally and preferably contains 60 percent, or greater, and more preferably 75 percent, or greater, $C_{10}+$ liquid hydrocarbons which boil above 160° C. (320° F.).

Cobalt-titania, and especially thoria promoted cobalt-titania catalysts exhibit high activity and selectivity in the conversion of carbon monoxide and hydrogen to $C_{10}+$ distillate fuels. The catalysts employed in the practice of this invention are prepared by techniques known in the art for the preparation of these and other catalysts. The catalyst can, e.g., be prepared by gellation, or cogellation techniques. Suitably, however, cobalt can be composited alone, or with the thoria, upon a previously pilled, pelleted, beaded, extruded, or sieved titania or titania-containing support material by the impregnation method. In preparing catalysts, the metal, or metals, is deposited from solution on the support to provide the desired absolute amount of the metal, or metals. Suitably, the cobalt is composited with the support by contacting the support with a solution of a cobalt-containing compound, or salt, e.g., a nitrate, carbonate or the like. The thoria, where thoria is to be added, can then be composited with the support in similar manner, or the thoria can first be impregnated upon the support, followed by impregnation of the cobalt. Optionally, the thoria and cobalt can be coimpregnated upon the support. The cobalt compounds used in the impregnation can be any organometallic or inorganic compound which decomposes to give cobalt oxide upon calcination, such as cobalt nitrate, acetate, acetylacetonate, naphthenate, carbonyl, or the like. Cobalt nitrate is especially preferred while cobalt halide and sulfate salts should generally be avoided. The salts may be dissolved in a suitable solvent, e.g., water, or hydrocarbon solvent such as acetone, pentane or the like. The amount of impregnation solution used should be sufficient to completely immerse the carrier, usually within the range from about 1 to 20 times the carrier by volume, depending on the concentration of the cobalt-containing compound in the impregnation solution. The impregnation treatment can be carried out under a wide range of conditions including ambient or elevated temperatures. Metal components other than thorium may also be added as promoters. Exemplary of such promoters are nickel, platinum, palladium, rhodium and lanthanium. In general, however, the addition of these metals have not been found to provide any significant benefit. In fact, surprisingly, the addition of copper and iron appear to have had a somewhat adverse effect upon the reaction. For this reason, the preferred catalyst is one which consists essentially of cobalt, or cobalt and thoria, dispersed upon the titania, or titania-containing support; or, in other words, catalysts which do not contain a significant amount of a metal, or metals, other than cobalt, or metals other than cobalt and thorium, dispersed upon the titania or titania-containing support.

Titania is used as a support, or in combination with other materials for forming a support. The titania used for the support, however, is necessarily one which contains a rutile:anatase ratio of at least about 2:3, and preferably at least about 3:2, as determined by x-ray diffraction. Preferably, the titania is one containing a rutile:anatase ratio ranging from about 3:2 to about 100:1, and greater, preferably from about 4:1 to about 100:1, and greater. The surface area of such forms of titania are less than about 50 m$^2$/g. This concentration of rutile provides generally optimum activity, and $C_{10}+$ hydrocarbon selectivity without significant gas and $CO_2$ make.

The catalyst, after impregnation, is dried by heating at a temperature above about 0° C., preferably between 0° C. and 125° C., in the presence of nitrogen or oxygen, or both, in an air stream or under vacuum. To obtain high activity, it is necessary to activate the cobalt-titania, or thoria promoted cobalt-titania catalyst prior to use. Preferably, the catalyst is contacted with oxygen, air, or other oxygen-containing gas at temperature sufficient to oxidize the cobalt and convert the cobalt to $Co_3O_4$. Temperatures ranging above about 150° C., and preferably above about 200° C. are satisfactory to convert the cobalt to the oxide, but temperatures above about 500° C. are to be avoided unless necessary for regeneration of a severely deactivated catalyst. Suitably, the oxidation of the cobalt is achieved at temperatures ranging from about 150° C. to about 300° C. The metal, or metals, contained on the catalyst are then reduced. Reduction is performed by contact of the catalyst, whether or not previously oxidized, with a reducing gas, suitably with hydrogen or a hydrogen-containing gas stream at temperatures above about 200° C.; preferably above about 250° C. Suitably, the catalyst is reduced at temperatures ranging from about 200° C. to about 575° C. for periods ranging from about 0.5 to about 24 hours at pressures ranging from ambient to about 40 atmospheres. A gas containing hydrogen and inert components in admixture is satisfactory for use in carrying out the reduction.

The cobalt, and thoria promoted cobalt-titania catalysts of this invention can be regenerated, and reactivated to restore their initial activity and selectivity after use by stripping the catalyst with a hydrocarbon solvent, or with a gas. Preferably the catalyst is stripped with a gas, most preferably with hydrogen, or a gas which is inert or non-reactive at stripping conditions such as nitrogen, carbon dioxide, or methane. The stripping removes the hydrocarbons which are liquid at reaction conditions. Gas stripping can be performed at substantially the same temperatures and pressures at which the reaction is carried out. Pressures can be lower however, as low as atmospheric. Temperatures can thus range from about 160° C. to about 290° C., preferably from about 190° C. to about 260° C., and pressures from about atmospheric to about 600 psig, preferably from about 140 psig to about 400 psig.

If it is necessary to remove coke from the catalyst, the catalyst can be contacted with a dilute oxygen-containing gas and the coke burned from the catalyst at controlled temperature below the sintering temperature of the catalyst. The temperature of the burn is controlled by controlling the oxygen concentration and inlet gas temperature, this taking into consideration the amount of coke to be removed and the time desired to complete the burn. Generally, the catalyst is treated with a gas having an oxygen partial pressure of at least about 0.1 psi, and preferably in the range of from about 0.3 psi to about 2.0 psi to provide a temperature ranging from about 300° C. to about 550° C., at static or dynamic conditions, preferably the latter, for a time sufficient to remove the coke deposits. Coke burn-off can be accomplished by first introducing only enough oxygen to initiate the burn while maintaining a temperature on the low side of this range, and gradually increasing the temperature as the flame front is advanced by additional oxygen injection until the temperature has reached optimum. Most of the coke can be readily removed in this way. The catalyst is then reactivated, reduced, and made ready for use by treatment with hydrogen or hydrogen-containing gas as with a fresh catalyst.

The invention will be more fully understood by reference to the following examples and demonstrations which present comparative data illustrating its more salient features. Feed compositions are expressed as molar ratios of the components.

The data given in the examples which follow were obtained in a small fixed bed reactor unit, gas chromatographic analytical data having been obtained during the runs which were conducted over various periods. All parts are in terms of weight units except as otherwise specified.

The "Schulz-Flory Alpha" is a known method for describing the product distribution in Fischer-Tropsch synthesis reactions. The Schulz-Flory Alpha is the ratio of the rate of chain propagation to the rate of propagation plus termination, and is described from the plot of ln (Wn/n) versus n, where Wn is the weight fraction of product with a carbon number of n. In the examples below, an Alpha value was derived from the $C_{10}/C_{20}$ portion of the product. The Alpha value is thus indicative of the selectivity of the catalyst for producing heavy hydrocarbons from the synthesis gas, and is indicative of the approximate amount of $C_{10}+$ hydrocarbons in the product. For example, a Schulz-Flory Alpha of 0.80 corresponds to about 35% by weight of $C_{10}+$ hydrocarbons in the product, a generally acceptable level of $C_{10}+$ hydrocarbons. A Schulz-Flory Alpha of 0.85, a preferred Alpha value, corresponds to about 54% by weight of $C_{10}+$ hydrocarbons in the products, and a Schulz-Flory Alpha of 0.90, a more preferred Alpha value, corresponds to about 74% by weight of $C_{10}+$ hydrocarbons in the product.

In the example which immediately follows a series of runs were conducted with several known Fischer-Tropsch catalysts, these being compared with a run using a cobalt-titania catalyst to demonstrate the particularly high effectiveness of the latter in converting synthesis gas to hydrocarbons.

EXAMPLE 1

A feed constituted of an admixture of carbon monoxide and hydrogen in molar ratio of $H_2:CO$ of 2:1 was contacted over a cobalt-titania catalyst (Catalyst A; 12% Co-$TiO_2$; ratio rutile:anatase=3.2) and several known cobalt catalysts, viz., 100 Co:5 $ThO_2$:8 MgO:200 kieselguhr (Catalyst B), 12% Co/$SiO_2$ (Catalyst C) and 25 Co:1.8 Ti:100 $SiO_2$ (Catalyst D), respectively, at temperature of 230° C., at a pressure of 150 psig, and at a space velocity of 400 $hr^{-1}$. The data shown in Table I demonstrate the level of CO conversion 70 hours after initiation of the runs, the $CO_2$ selectivity, $CH_4$ selectivity, $C_2+$ selectivity, and the Shulz-Flory Alpha value, which is a measure of the ability of a catalyst to produce $C_{10}+$ hydrocarbons.

TABLE I

Selectivity of Various Co Catalysts
T = 230° C., P = 150 psig, GHSV = 400 $hr^{-1}$ $H_2:CO$ = 2

|  | CO Conversion @ 70 Hours | $CO_2$ Select. Wt. % | $CH_4$ Select. Wt. % | $C_2+$ Select. Wt. % | Shulz-Flory Alpha |
|---|---|---|---|---|---|
| Catalyst A 12% Co/$TiO_2$ | 88 | 1.1 | 8.6 | 90.3 | 0.91 |
| Catalyst B 100 Co:5 $ThO_2$:8 MgO:200 KG[1] | 43 | 4.3 | 10.3 | 86.4 | — |
| Catalyst C 12% Co/$SiO_2$ | 72 | 1.6 | 8.7 | 89.7 | ~0.85 |
| Catalyst D 25 Co:1.8 Ti:100 $SiO_2$ | 21 | 1.9 | 13.8 | 84.3 | 0.74 |

[1]Prepared by procedure given at Page 137 and following: The Fischer-Tropsch and Related Syntheses, Storch, Golumbic and Anderson, John Wiley and Sons, Inc., New York (1951)

These data thus clearly show that Catalyst A, the Co/$TiO_2$ catalyst, is unique as regards its superior activity and selectivity. Moreover, the high Shulz-Flory Alpha value indicates an ability of this catalyst to produce in the product more than about 75% $C_{10}+$ hydrocarbons.

The rutile content of the $TiO_2$ support from which the catalyst is formed is significant, the CO conversion of the catalyst increasing as the rutile content of the $TiO_2$ support is increased. The following example demonstrates the effect of the rutile content of the $TiO_2$ supports from which cobalt-titania catalysts are formed, and the effects of the cobalt metal distribution upon the surface of the supports. In a first pair of runs, the rutile:anatase ratio of one support from which a catalyst is formed is 1.1:1 and the other has a rutile:anatase ratio of >30:1. In a second pair of runs, the rutile:anatase ratio of one support from which a catalyst is formed is 1.1:1, and the other >30:1.

EXAMPLE 2

Two 12% Co/$TiO_2$ catalysts were formed for use in a first pair of side-by-side runs by impregnating cobalt upon two portions of $TiO_2$ 16-20 mesh (Tyler) particles, the first portion having a rutile:anatase ratio of 1.1:1 and the other >30:1. Reference is made to Table II, Columns 2 and 3. Two additional portions of a 16-20 mesh (Tyler) $TiO_2$ were similarly impregnated with cobalt, the first having a rutile:anatase ratio of 1.1:1 and the other a rutile:anatase ratio of >30:1. Reference is made to Table II, Columns 4 and 5. The first pair of catalysts (Columns 2 and 3) were similarly dried, and then calcined in air for 3 hours at 250° C. The second pair of catalysts (Columns 4 and 5) were then similarly dried and then calcined in air for 3 hours at 500° C. These catalysts were then charged in equal quantities to the fixed bed reactor as previously described, reduced with hydrogen, and separate runs made with each catalyst at identical conditions, viz., 200° C., 280 psig, GHSV=1000 and H$_2$:CO of 2.15:1. The following data was taken after 20 hours operation, reference again being made to Table II.

TABLE II

Effect of Rutile Content,
and Cobalt Metal Dispersion, on 12% Co/TiO$_2$ Catalyst
16–20 Mesh, 200° C., 280 psig, GHSV = 1000 H$_2$/CO = 2.15

| TiO$_2$ Properties | | | | |
|---|---|---|---|---|
| Rutile:Anatase ratio, Wt. | 1.1:1 | >30:1 | 1.1:1 | >30:1 |
| Surface Area M$^2$/g | 36 | 10 | 33 | 10 |
| Pore Volume ml/g | 0.30 | 0.11 | 0.28 | 0.11 |
| Air Treat, °C. (3 Hrs.) | 250 | 250 | 500 | 500 |
| CO Conversion (@ 20 Hrs.) | 67 | 79 | 54 | 67 |
| Selectivity, mol. % | | | | |
| CH$_4$ | 9.7 | 11.5 | 9.9 | 11.7 |
| CO$_2$ | 0.2 | 0.7 | — | 0.3 |
| C$_2$+ | 90.1 | 87.8 | 90.1 | 88.0 |
| O$_2$ Chemisorption, μmol O$_2$/g catalyst | 213 | 265 | 178 | 202 |

The catalysts having the higher rutile content, or catalysts having the better cobalt metal dispersion (as measured by conventional O$_2$ chemisorption) are significantly more active in converting the CO and H$_2$ to hydrocarbons; albeit it will be noted, the gas and CO$_2$ content of the catalysts having the higher rutile content are slightly debited, and the C$_2$+ hydrocarbon content of the product slightly lower.

EXAMPLE 3

In another series of demonstrations, cobalt was dispersed on portions of 60–150 mesh (Tyler) titania by the heat decomposition of a cobalt carbonyl compound, CO$_2$(CO)$_8$; deposited from a pentane solution; a procedure described by reference to articles by A. S. Lisitsyn, V. L. Kuznetsov, and Yu. I. Ermakov entitled (1) "Catalysts Obtained By The Reaction of Transition-Element Organometallic Compounds With Oxide-Sypport Surfaces, Hydrogenation of Carbon Monoxide on Catalysts Supports" and (2) "Catalysts Obtained By The Reaction Of Transition Element Organometallic Compounds With Oxygen-Support Surfaces. Catalytic Properties of Systems Preposed By The Pyrolysis of Co(CO)$_8$ on Oxide Supports In The Reaction CO+H$_2$ Depending On Their Composition And Pretreatment" *Institute of Catalysis, Siberian Branch of the Academy of Sciences of the USSR, Novosibirsk.* Translated from Kinetika i Kataliz, Vol. 23, No. 4, pp 919–931, July–August, 1982. Two of these catalysts, referred to in columns two and three in Table III, were prepared from TiO$_2$ having a rutile:anatase ratio of 1:2.6, and are believed representative of prior art catalysts, and three of these catalysts referred to in columns four, five, and six were prepared from TiO$_2$ having a rutile:anatase ratio of >30:1. A sixth catalyst was prepared from cobalt nitrate, by impregnation of a TiO$_2$ support material havng a rutile:anatase ratio of >30:1 with a cobalt nitrate pentane solution. The several catalysts, each of which contained between 9.3 wt. % and 11.1 wt. % cobalt as shown by analysis, were pretreated (1) at temperatures approximating 250° C. for one hour in vacuum, or (2) in air at this temperature for three hours followed by a one hour period of treatment at 450° C. with hydrogen, or (3) with hydrogen at 450° C. for one hour, as shown in the Table. Reference is made to Table III.

TABLE III

60–150 Mesh Catalysts, 200° C., 280 psig, GHSV = 1000, H$_2$/CO = 2.15

| Wt. % Co | 9.3 | 10.1 | 8.7 | 9.2 | 9.6 | 11.1 |
|---|---|---|---|---|---|---|
| Co Compound | Carbonyl | Carbonyl | Carbonyl | Carbonyl | Carbonyl | Nitrate |
| Rutile:Anatase of TiO$_2$, Wt. | 1:2.6 | 1:2.6 | >30:1 | >30:1 | >30:1 | >30:1 |
| Pretreatment | 257° C.- 1 hr in vacuo | Air 250°- 3 hr H$_2$ 450°- 1 hr | 257° C.- 1 hr in vacuo | Air 250°- 3 hr H$_2$ 450°- 1 hr | H$_2$ 450°- 1 hr | Air 250°- 3 hr H$_2$ 450°- 1 hr |
| % CO Conversion | 30 | 5 | 59 | 97 | 93 | 95 |
| Mol % CH$_4$ Selectivity | 13.5 | 15.1 | 4.9 | 5.4 | 5.6 | 4.5 |
| O$_2$ Chemisorption, μmol O$_2$/g catalyst | — | 53 | — | 205 | 127 | 193 |

These data clearly show that the amount of conversion of the feed to hydrocarbons is very, very low with the catalysts prepared from a TiO$_2$ base containing a rutile:anatase ratio 1:2.6, viz., 30 percent when the catalyst is treated at 257° C. for 1 hour under vacuum as described by the reference procedure, supra. It is even poorer, viz., 5 percent, when the catalyst is pretreated with air and then reduced in accordance with the process of this invention. Methane make is very, very high in either instance, viz., 13.5 percent and 15.1 percent, respectively. The superior performance of the catalyst formed from the high rutile: anatase TiO$_2$ support is particularly manifest when the % CO conversions obtained with the catalyst formed from the low rutile::anatase ratio supports are compared with the catalyst formed from the high rutile:anatase TiO$_2$ supports (59%, 97%, 93%, and 95%, respectively). The CO conversion is poor because of the poor dispersion of the cobalt, as determined by the O$_2$-chemisorption data.

In pretreating a catalyst of this invention, wherein the cobalt of the starting cobalt carbonyl compound is dispersed on a TiO$_2$ base having a rutile:anatase ratio of >30:1, the performance of the catalyst is drastically improved. Pretreating in accordance with the reference procedure, the percent CO conversion to hydrocarbons is essentially doubled, viz., 59 percent vis-a-vis 30 percent, and methane make is drastically reduced, viz., from 13.5 percent to 4.9 percent. When the preferred pretreat of the present invention is employed, i.e., air activation followed by hydrogen reduction, the percent CO conversion rises to 97 percent, with only 5.4 percent methane production; and even when a similar catalyst is reduced without a preceding air treat, 93 percent CO conversion is obtained, with only 5.6 percent gas make.

The Co impregnated catalyst produced from a TiO$_2$ base having a rutile:anatase ratio of >30:1, pretreated with both air and hydrogen, provides 95 percent selectivity of the CO to hydrocarbons, with a gas make of only 4.5 percent.

The present process, utilizing the catalysts of this invention, is highly suitable for the conversion of synthesis gas to hydrocarbons. These catalysts are also useful for the conversion of methanol to hydrocarbons, as disclosed in our application Ser. No. 626,026, filed of even date herewith; the disclosure of which Application is herewith incorporated by reference. The reaction can be conducted in fixed bed, or slurry bed reactors with or without the recycle of any unconverted gas and/or liquid product. Total pressure is maintained over about 80 psig, preferably over about 140 psig, and the $H_2$:CO mole ratio of the reactant gases should be above about 0.5:1 and, preferably equal to or above about 2:1 to produce large amounts of $C_{10}+$ hydrocarbons. The $C_{10}+$ product is an admixture of linear paraffins and olefins which can be further refined and upgraded to high quality middle distillate fuels, or such other products as mogas, diesel fuel, jet fuel, lubes specialty solvents and the like. A premium grade middle distillate fuel of carbon number ranging from about $C_{10}$ to about $C_{20}$ can also be produced from the $C_{10}+$ hydrocarbon product. The catalyst is constituted of cobalt or cobalt and thorium supported on a rutile form of $TiO_2$ or rutile-titania-containing support which can contain such non-acidic materials as $SiO_2$, MgO, $ZrO_2$, $Al_2O_3$. The catalyst is preferably reduced with a $H_2$-containing gas at start-up.

It is apparent that various modifications and changes can be made without departing the spirit and scope of the present invention.

What is claimed is:

1. A process useful for the conversion of synthesis gas to hydrocarbons which comprises contacting at reaction conditions a feed comprised of an admixture of carbon monoxide and hydrogen, in $H_2$:CO molar ratio equal to or greater than about 0.5:1 at total pressure equal to or greater than about 80 psig, over a catalyst which comprises cobalt, or cobalt and thoria in catalytically active amount composited with titania or titania-containing support, wherein the titania support is one having a rutile:anatase ratio of at least about 2:3.

2. The process of claim 1 wherein the metal composited with the catalyst is cobalt, and the catalyst contains from about 2 percent to about 25 percent cobalt, based on the weight of the catalyst composition.

3. The process of claim 2 wherein the catalyst contains from about 5 to about 15 percent cobalt, based on the weight of the catalyst composition.

4. The process of claim 1 wherein both cobalt and thoria are composited with the catalyst, the catalyst containing from about 2 percent to about 25 percent cobalt, and from about 0.1 percent to about 10 percent thoria, based on the total weight of the catalyst.

5. The process of claim 4 wherein the catalyst consists from about 5 percent to about 15 percent cobalt, and from about 0.5 percent to about 5 percent thoria.

6. The process of claim 1 wherein the molar ratio of $H_2$:CO ranges from about 0.5:1 to about 4:1.

7. The process of claim 1 wherein the molar ratio of $H_2$:CO ranges from about 2:1 to about 3:1.

8. The process of claim 1 wherein the total pressure of the reaction ranges above about 140 psig.

9. The process of claim 1 wherein the total pressure of the reaction ranges from about 80 psig to about 600 psig.

10. The process of claim 1 wherein the reaction conditions are defined within ranges as follows:

| | |
|---|---|
| $H_2$:CO mole ratio | about 0.5:1 to 4:1 |
| Gas Hourly Space Velocities, V/Hr/V | about 100 to 5000 |
| Temperature, °C. | about 160 to 290 |
| Total Pressure, psig | about 80 to 600. |

11. The process of claim 10 wherein the reaction conditions are defined within ranges as follows:

| | |
|---|---|
| $H_2$:CO mole ratio | about 2:1 to 3:1 |
| Gas Hourly Space Velocities, V/Hr/V | about 300 to 1500 |
| Temperature, °C. | about 190 to 260 |
| Total Pressure, psig | about 140 to 400. |

12. The process of claim 1 wherein the catalyst, prior to reaction with the admixture of carbon monoxide and hydrogen, is activated by contact with an oxygen-containing gas to oxidize the cobalt and convert the cobalt to $Co_3O_4$, and the catalyst is then contacted with a reducing gas and the cobalt reduced.

13. The process of claim 12 wherein the cobalt is oxidized at a temperature above about 150° C.

14. The process of claim 13 wherein the cobalt is oxidized at temperatures ranging from about 150° C. to about 300° C.

15. The process of claim 12 wherein the cobalt is oxidized at a temperature above about 150° C., and the catalyst is then contacted with hydrogen or a hydrogen-containing gas and the cobalt reduced.

16. The process of claim 15 wherein the cobalt is oxidized at temperatures ranging from about 150° C. to about 300° C., and the cobalt is reduced at temperatures above about 200° C.

17. The process of claim 16 wherein the cobalt is reduced at temperatures ranging from about 200° C. to about 575° C.

18. The process of claim 1 wherein the rutile:anatase ratio of the titania support ranges from about 3:2 to about 100:1, or greater.

19. The process of claim 1 wherein the rutile:anatase ratio of the titania support ranges from about 4:1 to about 100:1, or greater.

20. The process of claim 1 wherein the rutile:anatase ratio of the titania support ranges from about 3:2 to about 100:1, or greater, and the catalyst contains from about 2 percent to about 25 percent cobalt, based on the weight of the catalyst composition.

21. The process of claim 20 wherein the catalyst contains from about 5 percent to about 15 percent cobalt.

22. The process of claim 1 wherein the rutile:anatase ratio of the titania support ranges from about 3:2 to about 100:1, or greater, the catalyst contains from about 2 percent to about 25 percent cobalt, based on the weight of the catalyst composition, and from about 0.1 percent to about 10 percent thoria, based on the weight of the catalyst composition.

23. The process of claim 22 wherein the cobalt and thoria are contained on the catalyst in Co:$ThO_2$ ranging from about 20:1 to about 1:1.

24. The process of claim 23 wherein the Co:$ThO_2$ ranges from about 15:1 to about 2:1.

* * * * *